US012582739B2

(12) United States Patent
Gable et al.

(10) Patent No.: US 12,582,739 B2
(45) Date of Patent: Mar. 24, 2026

(54) UVC AIR DISINFECTION DEVICE WITH LED THERMAL MANAGEMENT SYSTEM

(71) Applicant: DisinfectAir, LLC, Cuyahoga Falls, OH (US)

(72) Inventors: Richard M. Gable, Aurora, OH (US); David A. Bina, Northfield, OH (US); Thomas C. Bina, Northfield, OH (US); Janet Dorenkott, North Ridgeville, OH (US)

(73) Assignee: DisinfectAir, LLC, Cuyahoga Falls, OH (US)

( * ) Notice: Subject to any disclaimer, the term of this patent is extended or adjusted under 35 U.S.C. 154(b) by 363 days.

(21) Appl. No.: 17/900,083

(22) Filed: Aug. 31, 2022

(65) Prior Publication Data

US 2023/0068382 A1     Mar. 2, 2023

Related U.S. Application Data

(60) Provisional application No. 63/239,429, filed on Sep. 1, 2021.

(51) Int. Cl.
*A61L 9/20* (2006.01)

(52) U.S. Cl.
CPC ............. *A61L 9/20* (2013.01); *A61L 2209/12* (2013.01)

(58) Field of Classification Search
None
See application file for complete search history.

(56) References Cited

U.S. PATENT DOCUMENTS

| | | | |
|---|---|---|---|
| 10,221,857 B2 | 3/2019 | Niemiec et al. | |
| 10,670,026 B2 | 6/2020 | Niemiec et al. | |
| D893,072 S | 8/2020 | Niemiec et al. | |
| 2012/0273340 A1* | 11/2012 | Felix .................... | B01D 53/007 |
| | | | 204/157.3 |
| 2014/0030144 A1* | 1/2014 | Krosney .................. | A61L 9/20 |
| | | | 422/4 |

(Continued)

FOREIGN PATENT DOCUMENTS

| | | | | |
|---|---|---|---|---|
| CN | 106183453 B | * 11/2018 | ........ | B41J 11/00214 |
| KR | 20120053355 A | * 5/2012 | ............... | A61L 9/20 |

(Continued)

OTHER PUBLICATIONS

Efficient Power Tech "Cleanse—Retrofit Troffer" Retrieved online on Aug. 9, 2022 from https://www.efficientpowertech.com/retrofit-troffer/.

(Continued)

*Primary Examiner* — Andrew Smyth
(74) *Attorney, Agent, or Firm* — Eschweiler & Potashnik, LLC

(57)     ABSTRACT
A thermal management system for extending the life and operational effectiveness of UVC LEDs utilized in an air disinfection device, includes a hollow airflow chamber having a first end and a second end on opposite sides of a length of the hollow airflow chamber; a fan configured to generate airflow through the airflow chamber; a UVC LED array coupled to a framework, the framework including cut-outs for airflow, and the framework is coupled to the hollow airflow chamber in the path of the airflow. An air disinfection system and ceiling light troffer fixture are described herein.

20 Claims, 12 Drawing Sheets

(56) References Cited

U.S. PATENT DOCUMENTS

2019/0360680 A1* 11/2019 Niemiec .................. F21V 9/08
2019/0364634 A1* 11/2019 Shan ..................... F21V 19/005
2020/0354513 A1   11/2020 Niemiec et al.

FOREIGN PATENT DOCUMENTS

KR      20180120837 A  * 11/2018  ................ H02J 7/00
KR      20180120840 A  * 11/2018  ......... B60H 1/00814
KR      20180120841 A  * 11/2018  ......... F21V 33/0088
KR      20180120842 A  * 11/2018  ................ H02J 7/00
KR      20180120843 A  * 11/2018  ................ H02J 7/00
KR      20180120845 A  * 11/2018  .............. F21V 29/00
KR      20180120846 A  * 11/2018  .............. F24F 13/20
KR      20180120847 A  * 11/2018  .............. F24F 13/20
KR      20180120848 A  * 11/2018  ............ A61L 9/205
KR      20180120850 A  * 11/2018  ................ H02J 7/00
KR      20180120851 A  * 11/2018  ................ H02J 7/00
KR      20180120852 A  * 11/2018  ......... B60H 1/00814
KR      20180120854 A  * 11/2018  ........... B60H 3/0071
KR      20180120858 A  * 11/2018  ............. A61L 9/205
KR      20180120859 A  * 11/2018  ............. F24F 3/166
KR      20180120860 A  * 11/2018  ........ H05B 33/0809
KR      20180120861 A  * 11/2018  ............. F21V 29/00

OTHER PUBLICATIONS

Energy Focus, Inc. "nUVo TOWER" Retrieved online on Aug. 9, 2022 from https://shop.energyfocus.com/collections/uv-c/products/nuvo-tower.
XtraLight LED Solutions "UVC Recessed Troffer" Believed to have been on sale since 2019. Retrieved online on Aug. 9, 2022 from https://www.xtralight.com/products/uvc-recessed-troffer/.

* cited by examiner

70

52

79

77

70

78

52

20

73

12

91

92

60

1110

42

60

1000

1000

1000

1002

1004

1008

1006

42

1012

1008

1110

1014

1010

1010

1020

UVC AIR DISINFECTION DEVICE WITH LED THERMAL MANAGEMENT SYSTEM

CROSS-REFERENCE TO RELATED APPLICATIONS

This application claims the benefit of priority of U.S. provisional application 63/239,429, filed Sep. 1, 2021, which is incorporated herein by reference.

FIELD

The technology disclosed herein relates to extending the life and disinfecting intensity of UVC (Ultra-Violet, Type C) radiation of LEDs (light emitting diodes) used to deactivate microbes in various types of air disinfecting devices.

BACKGROUND

Until recently, the main source of UVC radiation (UV light typically defined as having wavelengths of 200 nm to 290 nm) used in air disinfection devices was a mercury vapor arc tube. However, such mercury arc tubes present several disadvantages. Tube disposal (due to the toxic mercury), high heat generation, magnetic ballasts (which are being phased out), and short lifespans are just some examples of such issues.

Recently, manufacturers have identified the superiority of the LEDs over the mercury arc tubes, and have begun to utilize the LEDs in air disinfection devices. Common LEDs do not have high disinfection capabilities. UVC LEDs, that is, light emitting diodes, that emit light in the UVC spectrum are more powerful. However, UVC LEDs also have disadvantages. Such UVC-producing LEDs suffer from longevity issues. It was determined that a culprit of the short longevity was build up of heat and insufficient removal of waste heat from the diode case. Furthermore, an inefficient design in thermal management of the waste heat will cause immediate degradation of the UVC intensity as well as accelerated degradation in the expected service life of the LEDs.

SUMMARY

The following is a brief summary of subject matter that is described in greater detail herein. This summary is not intended to be limiting as to the scope of the claims.

A thermal management system for extending the life and operational intensity of the UVC radiation generating LEDs utilized in an air disinfection device includes: a airflow chamber having a first end and a second end on opposite sides of a length of the airflow chamber; a fan configured to generate airflow through the airflow chamber and coupled to the airflow chamber; and a UVC LED array coupled to a framework, the framework including cut-outs for airflow, the framework coupled to the airflow chamber in the path of the airflow. An air disinfection unit and combination air disinfection unit and lighting fixture are also provided.

A thermal management system for extending the life and operational effectiveness of UVC LEDs utilized in an air disinfection device, includes a airflow chamber having a first end and a second end on opposite sides of a length of the airflow chamber; a fan configured to generate airflow through the airflow chamber; a UVC LED array coupled to a framework, the framework including cut-outs for airflow, and the framework is coupled to the airflow chamber in the path of the airflow.

In some aspects, the techniques described herein relate to an air disinfection system, including: a airflow chamber having a first end and a second end on opposite sides of a length of the airflow chamber; a fan configured to generate airflow through the airflow chamber and coupled to the airflow chamber; and a UVC LED array coupled to a framework, the framework including cut-outs for airflow, the framework coupled to the airflow chamber in the path of the airflow.

In some aspects, the techniques described herein relate to a combination air disinfection and ceiling light troffer fixture, including: a airflow chamber having a first end and a second end on opposite sides of a length of the airflow chamber; a fan configured to generate airflow through the airflow chamber and coupled to the airflow chamber; a UVC LED array coupled to a framework, the framework including one or more cut-outs for airflow, the framework coupled to the airflow chamber in the path of the airflow; and one or more lighting lamps.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE FIGURES

FIG. 5b is an enlargement of the encircled area of FIG. 5a.

FIG. 8a is an isometric view of the thermal management system of FIG. 7a configured as a stand-alone air disinfection unit with power cord and base; and FIG. 8b is an isometric rotated view showing the back side of FIG. 8a.

DETAILED DESCRIPTION

Figure 1:
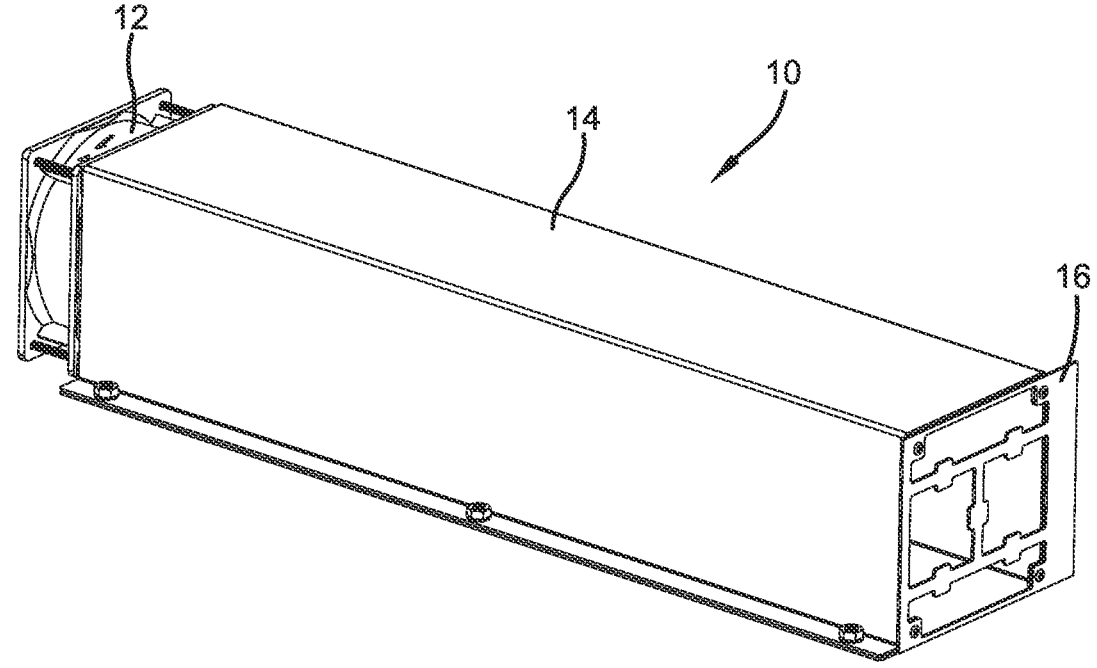
FIG. 1 is an isometric view of an exemplary thermal management system in accordance with the technology disclosed herein.

Various technologies pertaining to improvements in UV light disinfection technology are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something, and is not intended to indicate a preference.

The technology disclosed herein provides a novel thermal management system to eliminate waste heat produced by the LEDs during operation of various air disinfection devices whereby increasing life span and maintaining consistent levels of UVC radiation for disinfection. The system uses convection and conduction heat transfer that cooperate in a novel way to provide and maintain a means of heat removal from the UVC LED sources. Three different disinfecting device types that can utilize this improved system are disclosed as well: a ceiling troffer fixture, a combination ceiling light/disinfection unit, and a standalone disinfection unit. The system can be incorporated into any air disinfection device.

An exemplary system provided by the present technology disclosed herein includes a novel LED array component, affixed to a thermally conductive air chamber/enclosure and a mechanical fan for air movement through the air chamber and specifically through the LED array component.

One advantage provided by the system disclosed herein is that the novel array component of the present technology disclosed herein is constructed of a highly conductive material allowing waste heat from the LEDs to be removed both by conduction and convective thermal transfer. Other existing air disinfection systems utilizing LEDs as a source for UVC radiation, mount the LEDs to a substrate that is not thermally conductive, or is poorly conductive. In such designs, waste heat from the LEDs significantly degrade the operational intensity of the LEDs and the operational life expectancy of the LEDs.

Further, in an embodiment, the LED array is arranged perpendicular to the flow of air, as opposed to the customary parallel arrangement used in other designs. In an embodiment, the LED array is uniquely constructed with open sections allowing the airflow within the chamber to pass through the array as opposed to across the array increasing heat removal via convection.

By affixing the LED array component to the air chamber, which may also be constructed of a thermally conductive material, this allows waste heat from the array to travel conductively into the walls of the chamber. With active airflow through the chamber, the waste heat from the array drawn into the walls of the chamber by conduction is then removed via convection into the airflow stream and out of the disinfection unit.

In an embodiment, the air disinfection system can be utilized in multiple configurations (air disinfection type units) as disclosed herein. With an intake and exit for airflow, the thermal management system according to the teachings herein can be incorporated or configured into various forms of air disinfection device enclosures.

This description includes features relating to (1) a thermal management system used in an air disinfection device which utilizes LEDs for UVC radiation generation, (2) configurations of an LED array for the thermal management system, and (3) configurations of the thermal management system utilized in various UVC air disinfection devices.

With reference to FIG. 1, a thermal management system 10 in accordance with an exemplary embodiment of the technology disclosed herein includes: a fan 12, an airflow chamber 14, and a novel UVC LED array 16. The fan 12 is coupled to a first end of the airflow chamber 14. The LED array 16 is coupled to the opposite (second) end of the airflow chamber 14. The airflow chamber 14, as shown, is a hollow rectangular cylinder, but other hollow geometries, such as cylindrical, polygonal, or irregularly shaped can also be used.

In an embodiment, rather than opposite or first and seconds ends, the fan 12 and UVC LED array 16 can be on opposing portions of the airflow chamber, such as the fan 12 being within the 25% or 10% of the total length of the airflow chamber 14 that is nearest the first end (such as, 22% to 12% or 20% to 15%), and the UVC LED array 16 being within the 25% or 10% of the total length of the airflow chamber that is nearest the second end (such as, 22% to 12% or 20% to 15%).

Figure 2A:
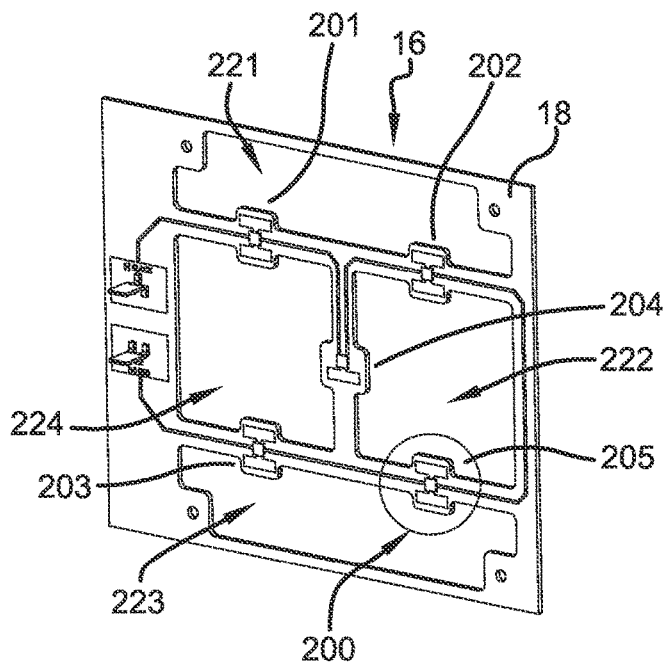
FIG. 2a is an isometric view of an exemplary UVC LED array.

The UVC LED array 16 is shown in more detail FIG. 2a. In this embodiment, the UVC LED array 16 has five UVC LEDs (first 201, second 202, third 203, fourth 204, and fifth 205) coupled (e.g., bonded) to a highly thermally conductive material (for example, aluminum) framework 18. The framework 18 is also coupled to the walls of the airflow chamber 14 in a thermally conductive manner and the walls may also be made of the highly conductive material. The UVC LED array refers to the entirety of the UVC LEDs and the framework refers to the substrate on which the UVC LEDs are coupled to. The term "coupled" has the common meaning in patent terminology, that is, including directly or indirectly attached.

Other embodiments, may have more or less than 5 UVC LEDs, such as, for example, 1 to 50, 3 to 25, or 4 to 15. The highly thermally conductive material may have a thermal conductivity of 100 W/m*K to 500 W/m*K, such as 200 W/m*K to 300 W/m*K, or 220 W/m*K to 280 as measured by SI guidelines.

The UVC LED array 16 has first, second, third, and fourth cut-outs 221, 222, 223, 224 that allow the air flow stream from the airflow chamber 14 to pass through the array 16 perpendicular to the face of the array 16. The cut-outs 221, 222, 223, 224, may comprise, for example, 10% to 90% of the cross-sectional area of the framework 18, such as 20% to 80%, or 30% to 70%. In an embodiment as shown, the framework 18 albeit with cut-outs covers the entire cross-sectional area of the airflow chamber 14. Thus, the totality area of the cut-outs 221, 222, 223, 224, may comprise, for example, 10% to 90% of the cross-sectional area of the hollow airflow chamber 14, such as 20% to 80%, or 30% to 70%. More generally, the total area of the totality of the one or more cut-outs may comprise, for example, 10% to 90% of the cross-sectional area of the hollow airflow chamber 14, such as 20% to 80%, or 30% to 70%.

In an embodiment, the UVC LED array and cut-outs are within at least 60 degrees of being perpendicular to the airflow, such as within 30 or 10 degrees of perpendicular. It should be noted that the term "cut-out" does not mean necessarily that material was necessarily cut away from the based material, a "cut-out" as used herein can be originally formed in the material (e.g., molded or cast with the opening).

The first cut-out 221 borders the first and second UVC LEDs 201, 202. The second cut-out 222 borders the second, fourth, and fifth UVC LEDs 202, 204, 205. The third cut-out 223 borders the third and fifth UVC LEDs 203, 205. The fourth cut-out 224 borders the first, third, and fourth UVC LEDs 201, 203, 204.

Figure 2B:
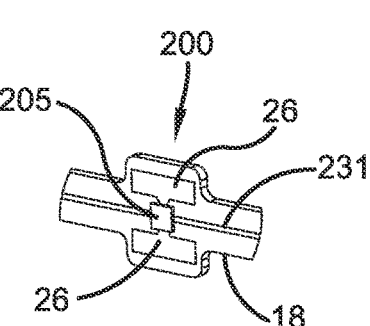
FIG. 2b is an enlargement of the encircled area of FIG. 2a labeled FIG. 2b.

FIG. 2b shows a zoomed-in view of the circled area 200 of FIG. 2. Each UVC LED 201-205 is bonded to the framework 18 of the array 16 as shown in FIG. 2b. The UVC LEDs 201-205 face the interior of the air flow chamber 14. Electrical contacts and/or traces 231 are also coupled to or embedded in the framework 18 to power the UVC LED lamp 24. Each UVC LED lamp 24 has one or more heat spreaders 26 associated with it to transfer heat from the UVC LED 24 to the framework 18. The heat spreaders 26 are also bonded to the framework 18 of the array 16. In an embodiment, the heat spreaders 26 are adjacent to at least one large cut-out (here the second and third cut-outs 222, 223. This design allows air flow generated from the fan 12 to efficiently contact and cool a high surface area of the UVC LEDs 201-205 and the framework 18.

Figure 3A:
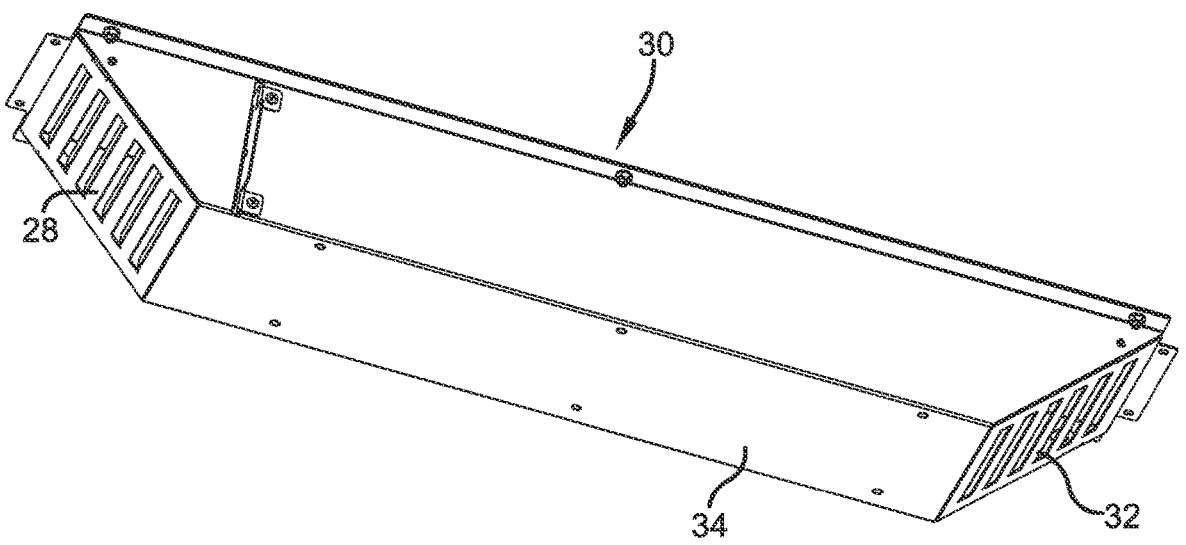
FIG. 3a is an isometric view of an air disinfection unit, configured for surface mounting.

FIG. 3a shows an embodiment of the air disinfection unit 30 configured for mounting to a surface. This can be mounted on wall or ceiling surfaces and powered by typical AC power routed to it behind the walls or ceiling. An intake vent 32 and exhaust vent 28 are coupled to opposite ends of the airflow chamber 34. This unit 30 can be attached to surfaces in indoor locations, such as, for example, hospital rooms, hospital hallways, offices, lobbies, elevators, restaurant dining areas, laboratories, school hallways or classrooms.

Figure 3B:
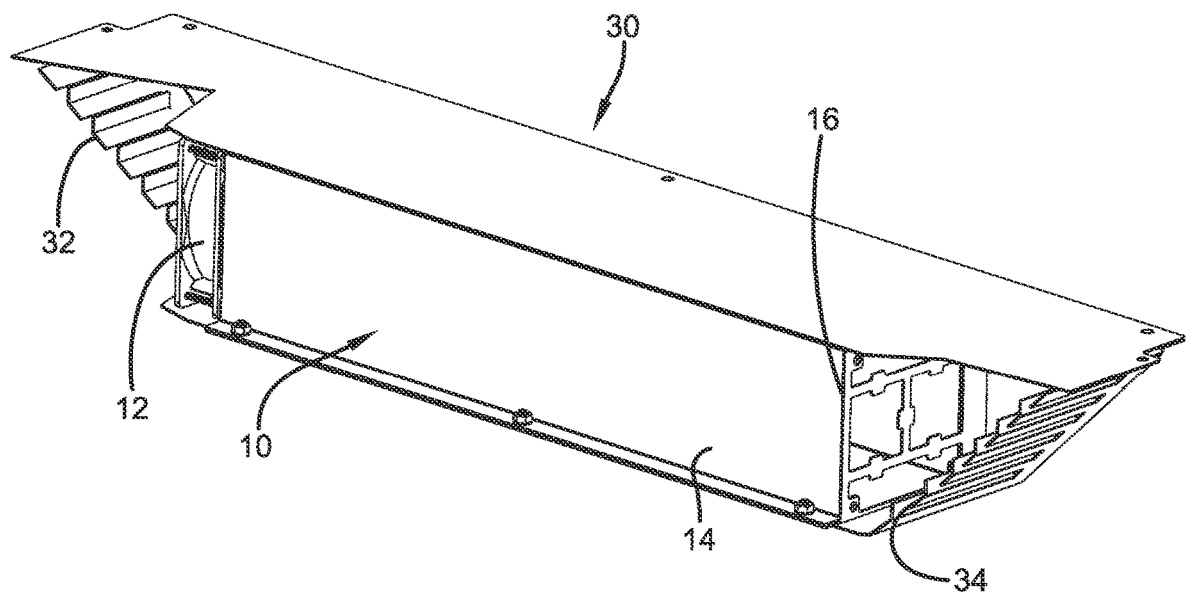
FIG. 3b is a cut away view of FIG. 3a showing the thermal management system within the unit.

FIG. 3b is a cut away view of FIG. 3a showing the thermal management system 10 within the unit 30. In an embodiment, the front and back outer walls of the airflow chamber 34 can form the front and back walls of the entire unit 30. In an embodiment, all walls forming the hollow airflow chamber 34 form the hollow airflow chamber 34 of the unit 30.

Figure 4:
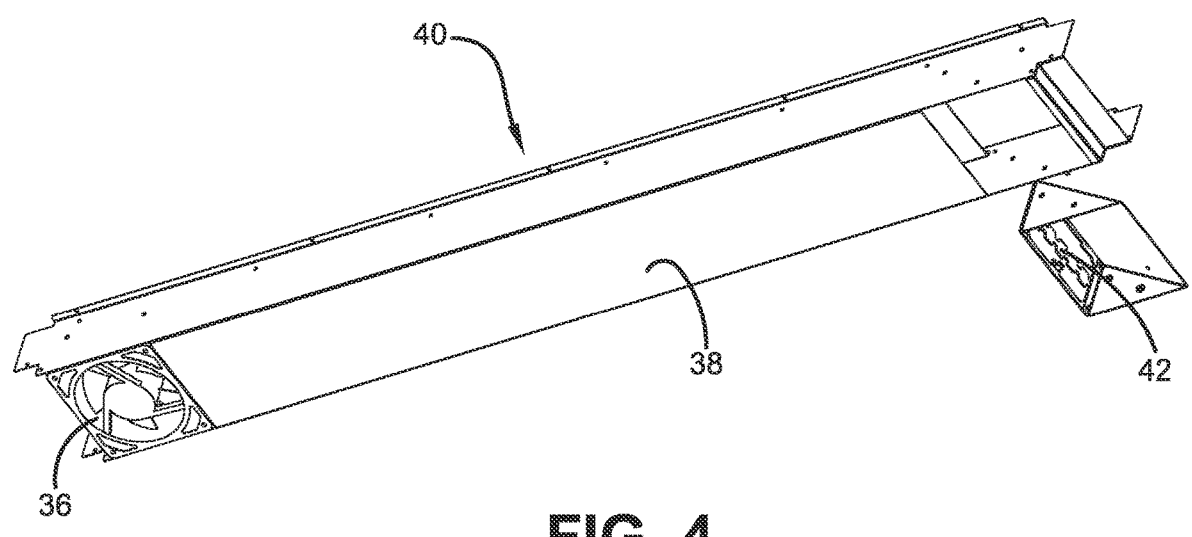
FIG. 4 is an isometric view of an exemplary thermal management system configured with horizontal fan intake, slender thermal chamber, and slender UVC LED array.
Figure 6A:
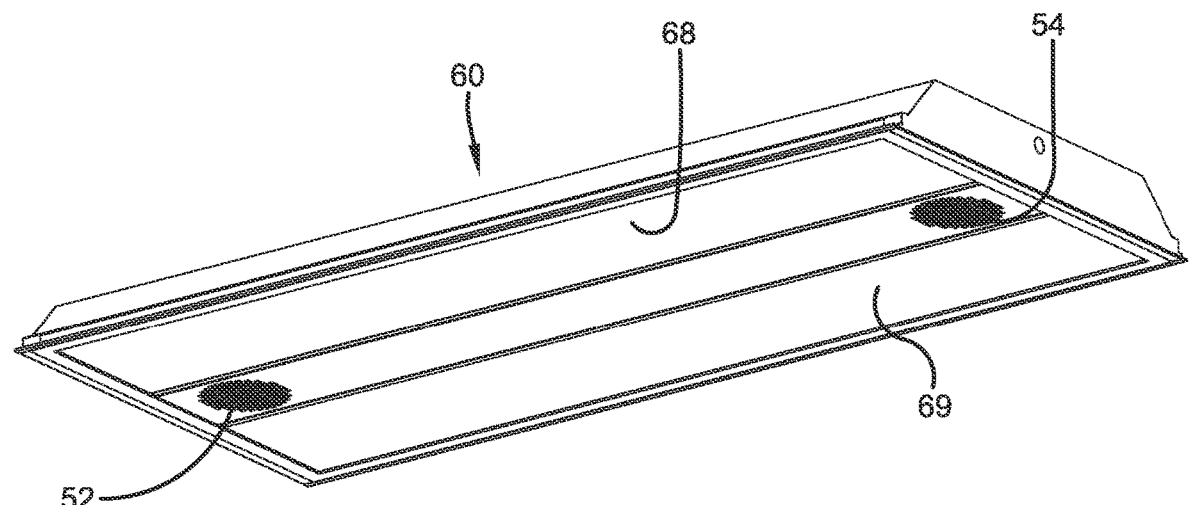
FIG. 6a is an isometric view of an air disinfection units configured as a ceiling grid type light fixture.

FIG. 4 is an exemplary air disinfection unit 40 configured with a horizontal fan intake 36 coupled to a slender hollow airflow chamber 38. By horizontal fan intake 36 it is meant that the fan and the intake opening is configured to be planar or substantially planar with the long dimension of the slender hollow airflow chamber 38. A slender UVC LED array 42 is coupled to the opposite end of the slender hollow airflow chamber 38. This embodiment employs a design that is shallow, allowing for a more compact insertion into various locations, such as, for example, a ceiling troffer as shown in FIG. 6a. With a shallow enough profile, a slender embodiment could even be placed within the interior of walls, e.g., about 3 to 5.5 inches or 3.25 to 3.75 inches in depth (depth meaning the deepest portion extending into the wall), and could either be disposed between interior opposing surfaces of a wall or anchored to the interior surface of the opposite facing wall with no part of the air disinfection unit 40 extending out of the wall. In an embodiment, the fan 36 or a vent covering the fan 36 would be no more than flush with the wall, as would the vent covering the LED array 42 and the exhaust. The LED array 42 is oriented to shine the major portion of the LED UVC light substantially parallel to the length (i.e., the longest dimension, running from the fan 36 to the LED array 42) of the hollow airflow chamber 38.

Figure 5A:
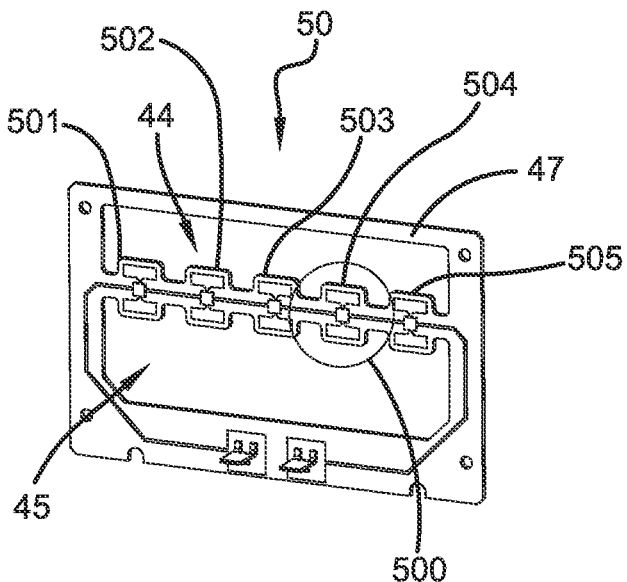
FIG. 5a is an isometric view of an exemplary LED array in a slender configuration.
Figure 5B:
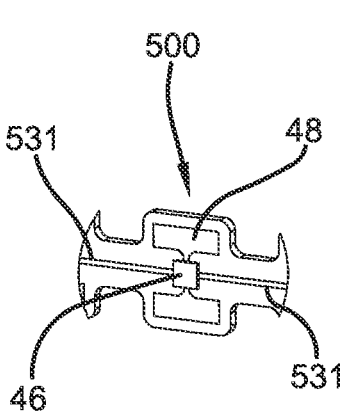

FIG. 5a is a more detailed view of an exemplary slender LED array 50; and FIG. 5b is an enlargement of the encircled area designated by area 500. Five UVC LEDs 46, each with heat spreaders 48 are coupled to the framework 47. As described above, the framework 47 is made of a material that rapidly conducts heat and upper and lower cut-outs 44, 45 are provided to cool the framework 47, heat spreaders 48, and UVC LEDs 46. Electrical contacts and traces are also coupled to or embedded in the framework to power the UVC LED lamps 46. The upper cut out 44 borders the top of each of the five UVC LEDs 501-505, and the lower cut out 45 borders the bottom of each of the five UVC LEDs 501-505.

In either the embodiment of FIG. 2a or 5a, at least two cut outs border the UVC LEDs.

Figure 6B:
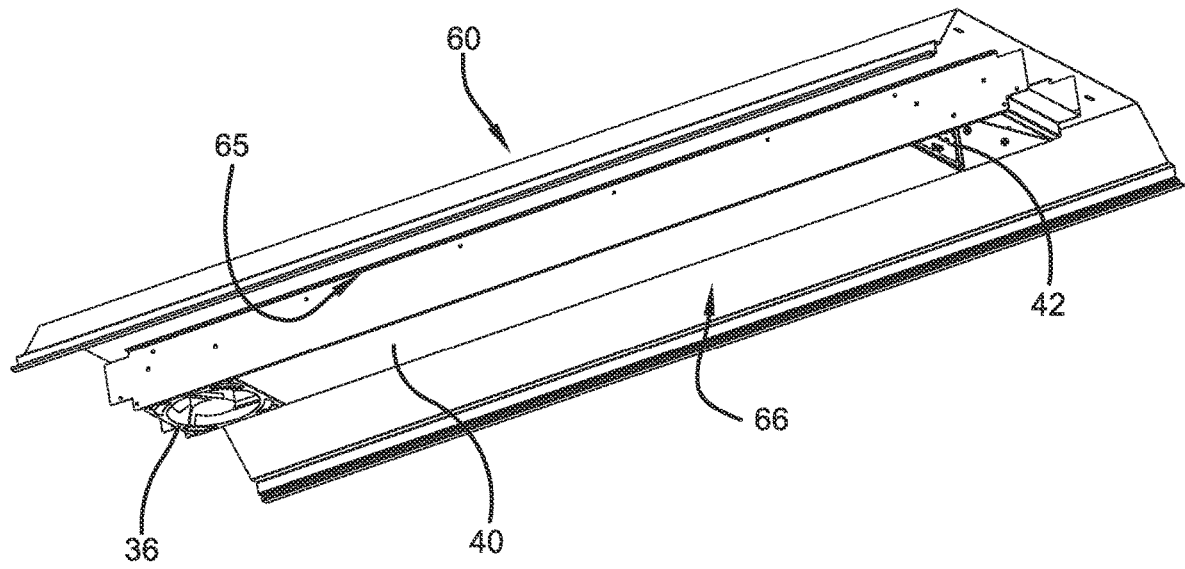
FIG. 6b is a view FIG. 6a without the cover assembly and end caps to show the thermal management system within.

FIG. 6a is an isometric view of an air disinfection unit configured as a ceiling troffer 60 (a ceiling grid type light fixture). FIG. 6b is a view of FIG. 6a without the cover assembly 61 and end caps 63 to show the thermal management system 40 within. The air disinfection unit 40 described above is in the center of the fixture 60, and optionally, one or more traditional bi pin fluorescent, bi pin incandescent, bi pin LED, or other lamps or lights can be positioned on either side in areas for light fixtures 65, 66. The intake vent 54 and exhaust vent 52 are visible, and in this embodiment are formed as a single panel that is coupled to the air disinfection unit. If extra disinfection is desired, the areas for light fixtures 65, 66 can be replaced with one or two additional air disinfection units 40. Windows 68, 69 are shown overlaying the light fixture area of the ceiling troffer 60.

Figure 7A:
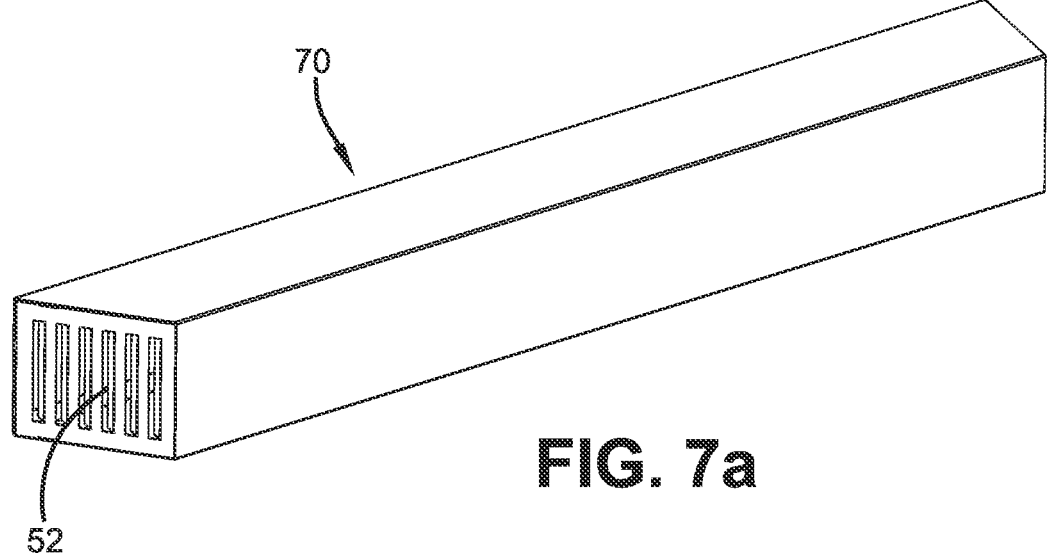
FIG. 7a is an isometric view of the thermal management system configured in another contemplated design.
Figure 7B:
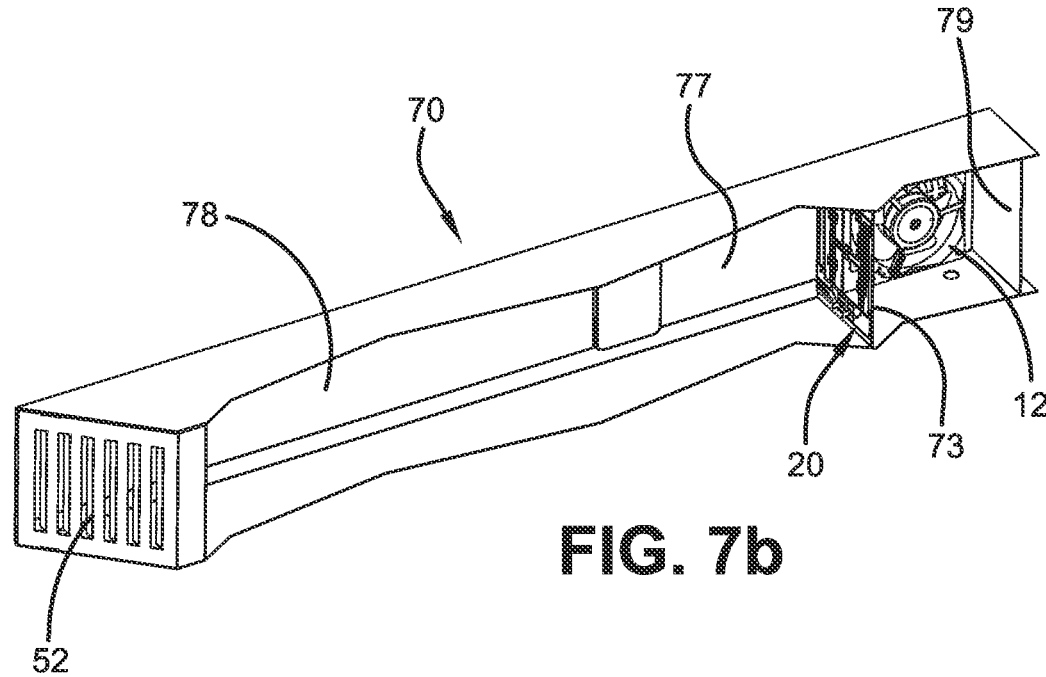
FIG. 7b is a cut away view of FIG. 7a showing the chamber, fan and array arrangement.

FIG. 7a is an isometric view of the air disinfection unit 70 configured in another contemplated design; and FIG. 7b is a cut away view of FIG. 7a showing the airflow chamber 78, fan 12 and UVC LED array 20. In this embodiment, the fan 12 is in a horizontal configuration that is orthogonal to the UVC LED array 20 and frame. The LED array 20 may be the same or similar to either FIG. 5A or 2A, or have some other geometry including one or more cut-outs and one or more UVC LEDs coupled to the frame.

A first terminal end of the unit 70 includes an end wall 79, and the fan 12 is coupled to and goes through an outer back panel 77. The outer back panel 77 and a length portion of the chamber 78 may be the same wall. Airflow enters at the fan and flows past the UVC LED array 20 and framework 73, cooling the LEDs. The top face of the UVC LEDs face the length portion (i.e. the longest direction of the chamber, running from the fan to the UVC LED array) of the airflow chamber 78, disinfecting the air as it flows through the chamber 78. In other words, the UVC LEDs are aligned with the length of the airflow chamber and the direction of air flow, or to further clarify, the UVC LEDs are configured to emit at least the majority of the light they produce in the direction of the length of the airflow chamber. This contrasts with devices that have LEDs that face orthogonally to the airflow, where dwell time in the UVC light is reduced.

In an embodiment, the air disinfection unit 70 is configured to have an airflow chamber that encompasses a volume of 1 to 50 cubic feet, such as, for example, 2 to 10, or 3 to 6 cubic feet. In an embodiment, the fan is configured to move 1 to 1000 cubic feet/minute, such as, for example, 10 to 100 cubic feet/minute, or 3 to 10 cubic feet/minute. Similarly, the air disinfection unit 70 is configured to effectively disinfect a volume of 1 to 50 cubic feet, such as, for example, 2 to 10, or 3 to 6 cubic feet.

Figures 8A, 8B:
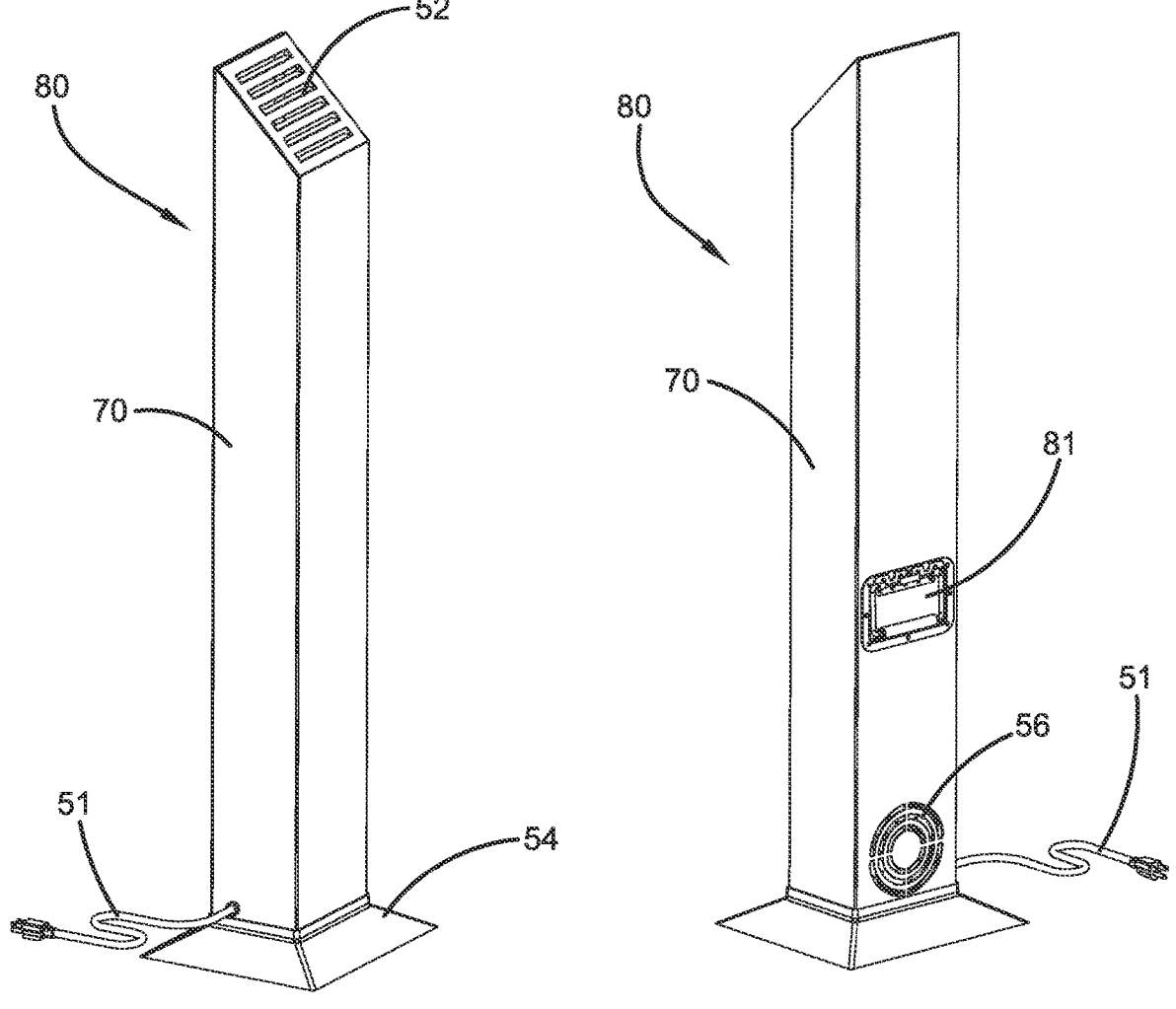

FIG. 8a is an isometric view of the air disinfection unit 70 of FIG. 7a configured as a free-standing, stand-alone air disinfection unit with power cord 51 and base 54; and FIG. 8b is an isometric rotated view showing the back side of FIG. 8a. An intake vent 56 is operatively associated with the fan 12 and extends through the outer back panel of the unit 80. A handle 81 is also disposed on the rear panel. A control panel (not shown) is also coupled to the device, to control off/on, fan speed, and optional LED intensity.

In an embodiment, LED intensity may be configured to automatically increase with increasing fan speed, and vice-versa, to ensure appropriate disinfection at higher through-puts/volumes.

The components of the units disclosed herein can be assembled by fasteners, extrusion, molding, adhering, or other technology. In particular the airflow chamber can be manufactured by aluminum extrusion and can be anodized or powder coated. The intake and exhaust vents can simply be slots machined into the outer panels. The supports at the base can be made of ⅛" thick laser cut aluminum plate and can be removable for ease in shipping/packaging.

Figures 9, 10A, 10B, 10C:
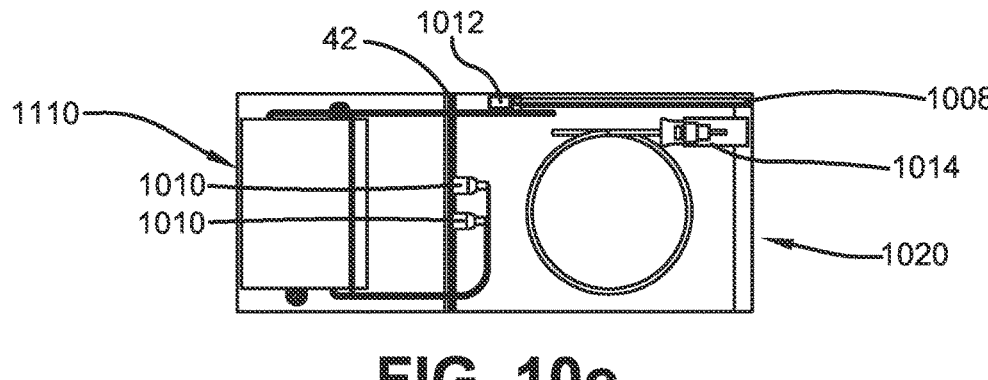
FIG. 9 is an isometric view of an embodiment of a ceiling troffer for use with the thermal management system and air disinfection system disclosed herein.
FIG. 10a is a cut-away view of an example ceiling troffer unit.
FIG. 10b is a zoomed-in view of a portion of FIG. 10a showing various wiring and electrical features.
FIG. 10c is a second zoomed-in view of a portion of FIG. 10a showing various wiring and electrical features.

FIG. 9 shows an additional isometric view of an embodiment of the ceiling troffer 60 with details for the power input location. Power i.e., lines for conducting electricity, can enter the unit through a side location 92 near the LED array, or through a location on the top of the ceiling troffer 60 In an embodiment, the max power is 80 Watts at 120 Voltage. In an embodiment, a wire management channel is utilized to guard the wiring from degradation from UV-C radiation during operation. The wire management channel can also allow field installation of the troffer fixture per NFPA guidelines. The wire management channel may be formed of metal and run the length of the hollow airflow chamber guarding the wiring from the UVC light.

FIGS. 10a, 10b, and 10c show cut-away and zoomed-in views of an embodiment of the ceiling troffer 60 showing wiring details. In FIG. 10a the troffer 60 is shown including the LED array 42 and the driver 1110 for the LED array. Detail view 1000 is shown in FIG. 10b and zoomed-in view 1020 is shown in FIG. 10c.

FIG. 10B shows a zoomed in view of area designated by 1000 in FIG. 10b. The power line for the fan 1004, the line and neutral conductors from the lamp holders 1006 and the line and neutral extension 1008 are shown with crimp on connectors 1002 coupling these.

FIG. 10C shows a zoomed in view of the area designated by zoomed-in view 1020 in FIG. 10a. The driver 1110 is electrically coupled to the LED array 42 via a quick connect wiring adaptor. The line and neutral extension 1008 are shown connected with crimp on connectors 1012 to the driver 1110. The input power connector/terminal block of the ceiling troffer 60 fixture is also shown.

Figure 11:
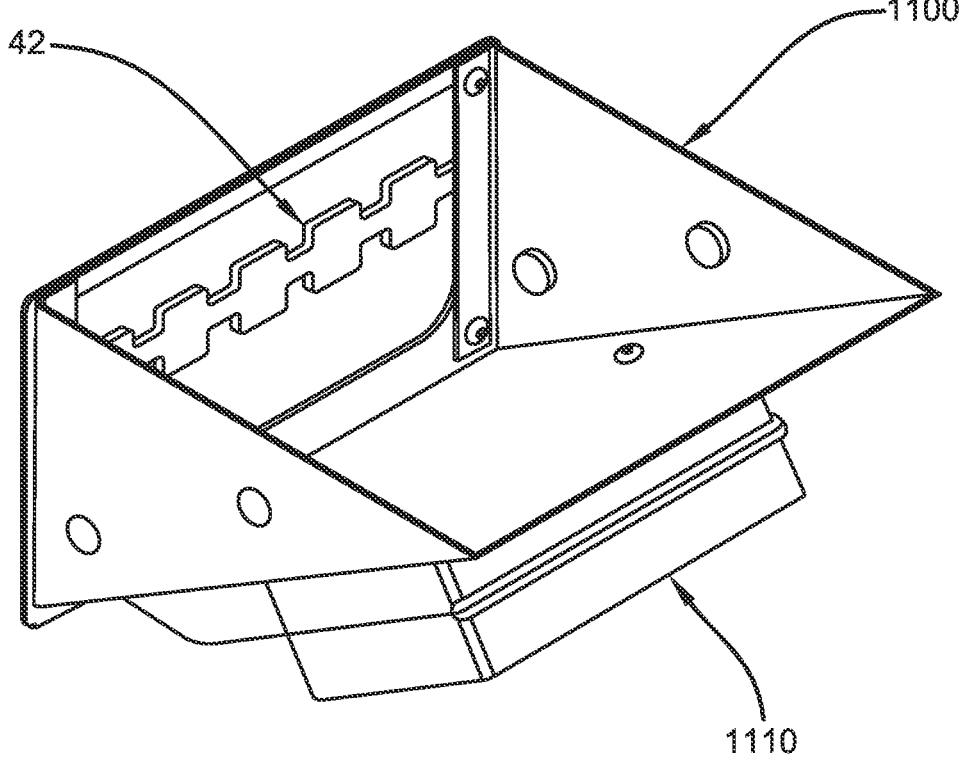
FIG. 11 is an detailed view of a bracket and driver component supporting the UVC LED array.

FIG. 11 shows an isometric view of a slender UVC LED array 42 and a bracket 1100 for holding the UVC LED array 42. The bracket 1100 is configured to be coupled to the end of the airflow chamber and is angled, e.g. at 30 to 60 degrees, or 35 to 55 degrees, or 40 to 45 degrees. A driver 1110 for the LED array 42 is coupled to the bracket 1100 on the side opposite the LED array 42. In an embodiment, the fan is of an all-metal construction or at least the fan blades and other parts facing the UVC light are all metal to avoid degradation from the UVC light.

In an embodiment, the interior of the hollow air chamber is reflective so as to reflect the UVC light within the chamber. The reflective surface may be a smoothly polished aluminum, copper, silver, or gold surface.

In the thermal mitigation system for air disinfection disclosed herein, the UVC LED array, thermally conductive material, the airflow chamber and fan cooperate to form a highly efficient means of removing the waste heat generated by the UVC LEDs to significantly increase the efficiency, longevity, intensity, and operational life of the UVC LEDs over other devices.

In an embodiment, a filter just before or just after the fan may be included in the airflow path to minimize dust accumulation in the airflow chamber and on the LEDs, as well to further purify the air.

In an embodiment a method for disinfecting air comprises the steps of: forcing air through an airflow chamber, contacting the air with UVC light from a UVC LED, dispersing heat from the UVC LED into a heat spreader and then into a heat conductive framework and/or the surrounding airflow chamber.

The term "hollow" as used herein, means completely (except for the framework and LED array) or substantially hollow such as to allow airflow through it relatively unimpeded. The framework and LED array are included within the hollow airflow chamber, and other items could be included too within the meaning of hollow.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. If not specified above, the properties mentioned herein may be determined by applicable ASTM standards, or if an ASTM standard does not exist for the property, the most commonly used standard known by those of skill in the art may be used. The articles "a," "an," and "the," should be interpreted to mean "one or more" unless the context indicates the contrary.

What is claimed is:

1. A thermal management system for UVC LEDs utilized in an air disinfection device, comprising:
   an airflow chamber having a first end and a second end on opposite sides of a length of the airflow chamber;
   a fan configured to generate airflow through the airflow chamber; and
   a UVC LED array coupled to a framework, the framework including cut-outs for airflow, the cut-outs comprising a first cut-out and a second cut-out; the framework coupled to the airflow chamber in a path of the airflow;

wherein UVC LEDs of the UVC LED array are configured to emit light in a longest direction of the airflow chamber;

wherein the fan is coupled to the airflow chamber within 25% of a total length of the airflow chamber nearest the first end, and the UVC LED array is within 25% of the total length of the airflow chamber that is nearest the second end of the airflow chamber; and wherein a UVC LED of the UVC LED array is between a first heat spreader and a second heat spreader, the first heat spreader borders the first cut-out on a first side of the UVC LED and the second heat spreader borders the second cut-out on an opposite side of the UVC LED; and wherein at least one UVC LED is attached to at least one dedicated heat spreader that is not attached to another UVC LED; and wherein at least one dedicated heat spreader extend perpendicularly to a length direction of the airflow chamber on a protrusion of the framework into at least one of the cut-outs.

2. The thermal management system of claim 1, wherein the fan is coupled to the airflow chamber within 10% of a total length of the airflow chamber nearest the first end, and the UVC LED array is within 10% of the total length of the airflow chamber that is nearest the second end of the airflow chamber.

3. The thermal management system of claim 1, wherein the fan is coupled to the airflow chamber at the first end and the UVC LED array is coupled to the airflow chamber at the second end of the airflow chamber.

4. The thermal management system of claim 1, wherein the framework coupled to the UVC LED array comprises a material with a thermal conductivity of 100 W/m*K to 500 W/m*K.

5. The thermal management system of claim 1, wherein each UVC LED of the UVC LED array is between two heat spreaders, and each heat spreader borders at least one of the cut-outs.

6. The thermal management system of claim 1, where the UVC LED array is within 60 degrees of being perpendicular to the airflow.

7. The thermal management system of claim 1, wherein the cut-outs comprise 10% to 90% of a cross-sectional area of the framework.

8. An air disinfection system, comprising:

an airflow chamber having a first end and a second end on opposite sides of a length of the airflow chamber;

a fan configured to generate airflow through the airflow chamber and coupled to the airflow chamber; and a UVC LED array comprising a plurality of UVC LEDs coupled to a framework, the framework including cut-outs for airflow, the framework coupled to the airflow chamber in a path of airflow;

wherein a top face of a UVC LED of the UVC LED array is aligned with the length of the airflow chamber so as to emit light in a longest direction of the airflow chamber;

wherein at least one UVC LED is attached to at least one dedicated heat spreader that is not attached to another UVC LED and the at least one dedicated heat spreader is bordered by at least one of the cut-outs; and wherein at least one dedicated heat spreader extend perpendicularly to a length direction of the airflow chamber on a protrusion of the framework into at least one of the cut-outs.

9. The air disinfection system of claim 8, wherein at least one UVC LED is attached to at least two dedicated heat spreaders that are not attached to another UVC LED and the at least two dedicated heat spreaders are bordered by at least one of the cut-outs.

10. The air disinfection system of claim 8, wherein the fan is configured to move 1 to 1000 cubic feet/minute, and the UVC LED array is configured to effectively disinfect 1 to 1000 cubic feet/minute of air.

11. A combination air disinfection and ceiling light troffer fixture, comprising:

an airflow chamber having a first end and a second end on opposite sides of a length of the airflow chamber;

a fan configured to generate airflow through the airflow chamber and coupled to the airflow chamber;

a UVC LED array coupled to a framework, the framework including one or more cut-outs for airflow, the cut-outs comprising a first cut-out and a second cut-out, the framework coupled to the airflow chamber in a path of airflow; and one or more lighting lamps;

wherein a top face of a UVC LED of the UVC LED array is aligned with the length of the airflow chamber so as to emit light in a length direction of the airflow chamber;

wherein the fan is coupled to the airflow chamber within 25% of a total length of the airflow chamber nearest the first end, and the UVC LED array is within 25% of the total length of the airflow chamber that is nearest the second end of the airflow chamber; and wherein a UVC LED of the UVC LED array is between a first heat spreader and a second heat spreader, the first heat spreader borders the first cut-out on a first side of the UVC LED and the second heat spreader borders the second cut-out on an opposite side of the UVC LED; and wherein at least one UVC LED is attached to at least one dedicated heat spreader that is not attached to another UVC LED; and wherein at least one dedicated heat spreader extend perpendicularly to a length direction of the airflow chamber on a protrusion of the framework into at least one of the cut-outs.

12. The combination air disinfection and ceiling light troffer fixture of claim 11, wherein the lighting lamps are LED bi pin lamps.

13. The combination air disinfection and ceiling light troffer fixture of claim 11, wherein the fan is configured to move 1 to 1000 cubic feet/minute, and the UVC LED is configured to effectively disinfect 1 to 1000 cubic feet/minute of air.

14. The combination air disinfection and ceiling light troffer fixture of claim 11, wherein at least one UVC LED of the UVC LED array is coupled to at least two heat spreaders that are coupled to the framework.

15. The combination air disinfection and ceiling light troffer fixture of claim 11, wherein the cut-outs comprise 10% to 90% of a cross-sectional area of the airflow chamber.

16. The combination air disinfection and ceiling light troffer fixture of claim 11, wherein the fan is coupled to the airflow chamber within 1025% of a total length of the airflow chamber nearest the first end, and the UVC LED array is within 10% of the total length of the airflow chamber that is nearest the second end of the airflow chamber.

17. The thermal management system of claim 1, wherein the UVC LED array comprises first, second, third, fourth, and fifth UVC LEDs; and the cut-outs further comprise third and fourth cut-outs; wherein the first cut-out borders the first and the second UVC LEDs, the second cut-out borders the second, fourth, and fifth UVC LEDs, the third cut-out borders the third and fifth UVC LEDs, and the fourth cut-out borders the first, third, and fourth UVC LEDs.

18. The thermal management system of claim 1, wherein UVC LED array comprises first and second UVC LEDs; wherein the first cut-out borders a first side of each of the first and second UVC LEDs, and the second cut-out borders a second side of each of the first and second UVC LEDs.

19. The air disinfection system of claim 8, wherein at least two cut-outs border at least the first and second heat spreader of the UVC LEDs.

20. The combination air disinfection and ceiling light troffer fixture of claim 11, wherein the UVC LED array comprises first, second, third, fourth, and fifth UVC LEDs; and the cut-outs further comprise third and fourth cut-outs; wherein the first cut-out borders the first and the second UVC LEDs, the second cut-out borders the second, fourth, and fifth UVC LEDs, the third cut-out borders the third and fifth UVC LEDs, and the fourth cut-out borders the first, third, and fourth UVC LEDs; or wherein UVC LED array comprises first and second UVC LEDs; wherein the first cut-out borders a first side of each of the first and second UVC LEDs, and the second cut-out borders a second side of each of the first and second UVC LEDs.

\* \* \* \* \*